United States Patent [19]

Whistler

[11] Patent Number: 5,445,678
[45] Date of Patent: Aug. 29, 1995

[54] SUBGRANULAR CRYSTALLINE STARCH AS FAT SUBSTITUTE

[76] Inventor: Roy L. Whistler, 320 Laurel Dr., West Lafayette, Ind. 47906

[21] Appl. No.: 86,227

[22] Filed: Jul. 1, 1993

Related U.S. Application Data

[63] Continuation of Ser. No. 706,894, May 29, 1991, abandoned.

[51] Int. Cl.⁶ .................... C08B 30/12; A23L 1/05
[52] U.S. Cl. ........................... 127/67; 127/32; 426/661; 426/804
[58] Field of Search .................. 127/32, 67; 426/661, 426/804

[56] References Cited

U.S. PATENT DOCUMENTS

| | | | |
|---|---|---|---|
| 3,023,104 | 2/1962 | Battista | 426/549 |
| 3,351,489 | 11/1967 | Battista | 127/32 |
| 3,666,557 | 5/1972 | Jensen et al. | 127/32 |
| 3,922,197 | 11/1975 | Leach et al. | 435/96 |
| 3,922,198 | 11/1975 | Kuske et al. | 435/96 |
| 3,962,465 | 6/1976 | Richter et al. | 426/48 |
| 3,986,890 | 10/1976 | Richter et al. | 127/28 |
| 4,072,535 | 2/1978 | Short et al. | 127/32 |
| 4,308,294 | 12/1981 | Rispoli et al. | 426/564 |
| 4,393,202 | 7/1983 | Breuninger | 536/102 |

(List continued on next page.)

FOREIGN PATENT DOCUMENTS

| | | | |
|---|---|---|---|
| 770089 | 3/1957 | United Kingdom | 536/102 |
| 83/00007 | 2/1983 | WIPO . | |
| 91/01029 | 9/1991 | WIPO . | |

OTHER PUBLICATIONS

*Colloidal Macromolecular Phenomena. Part II. Novel Microcrystals of Polymers*, Journal of Applied Polymer Science, vol. 11, pp. 481–498 (1967).

*Colloids: Particle Gels*, by Eric Dickinson, *Chemistry & Industry*, Oct. 1990, pp. 595–599.

*Paselli SA2*, AVEBE Product Information Ref. No. 05.12.31.167 EF, AVEBE b.a. International Marketing and Sales, Foxhol, Holland, Jun. 1988.

"Scanning Electron Microscopy of Enzyme Digested Varagu Starch Granules", Paramahans, S. V. and Tharanathan, R. N., *Starch/Starke*, 34 (1982) no month available Nr. 3, S. 73–76.

"Degradation of Starch Granules by Alpha–Amylase of Streptomyces precox NA–273", Takaya, T., Sugimoto, Y., Wako, K. and Fuwa, H., *Starch/Starke*, 31 (1979) no month available Nr. 6, S. 205–208.

"Scanning Electron–Microscopy of Starch Granules (List continued on next page.)

*Primary Examiner*—Paul Lieberman
*Assistant Examiner*—Patricia Hailey
*Attorney, Agent, or Firm*—Barnes & Thornburg

[57] ABSTRACT

A microcrystalline starch composition is prepared by disintegration of microporous starch granules produced by partial hydrolysis of granular starch. The composition finds use particularly as a fat substitute in reduced calorie foods. The starch composition is optionally treated with starch reactive cross-linking agents and/or other surface modifying agents to optimize its rheological properties and the organoleptic qualities of processed foods containing the microcrystalline starch composition.

7 Claims, No Drawings

U.S. PATENT DOCUMENTS

| | | | |
|---|---|---|---|
| 4,492,714 | 1/1985 | Cooper et al. | 426/602 |
| 4,510,166 | 4/1985 | Lenchin et al. | 426/565 |
| 4,551,177 | 11/1985 | Trubiano et al. | 106/210 |
| 4,585,858 | 4/1986 | Molotsky | 536/4.1 |
| 4,615,892 | 10/1986 | Morehouse et al. | 426/250 |
| 4,911,946 | 3/1990 | Singer et al. | 426/589 |
| 4,917,915 | 4/1990 | Cain et al. | 426/573 |
| 4,985,082 | 1/1991 | Whistler | 426/661 |
| 5,051,271 | 9/1991 | Iyengar et al. | 426/658 |
| 5,275,837 | 1/1994 | Eastman | 426/661 |

OTHER PUBLICATIONS

With Or Without Amylase Attack", Fuwa, H., Sugimoto, Y., and Takaya, T.

"Susceptibility of Various Starch Granules to Amylases as Seen by Scanning Electron Microscope", Fuwa, H., Sugimoto, Y., Tanaka, M., Glover, D. V. *Staerke* 1979, no month available 30(6), 186–91 (Abstract).

"Degradation of Various Starch Granules by Glucoamylases of Rhizopus Amagasakiens, Rhizopus Niveus, and Endomyces", Takaya, T., Glover, D. V., Sugimoto, Y., Tanaka, M., Fuwa, H., *Denpun Kagaku,* 1982, 29(4), 287–93 (Abstract).

"Hydrolysis of Large and Small Starch Granules From Normal and Waxy Barley Cultivars by a–Amylases From Barley Malt", MacGregor, A. W., Ballance, D. L., *Cereal Chem.,* 1980, no month available 57(6), 397–402 (Abstract).

"Amyloglucosidase-catalysed Erosion of Native, Surface-modified and Chlorine-treated Wheat Starch Granules. The Influence of Surface Protein", Greenwell, P., Evers, A. D., Gough, B. M., and Russell, P. L., *Journal of Cereal Science,* 3, no month available (1985), 279–293 (Abstract).

SUBGRANULAR CRYSTALLINE STARCH AS FAT SUBSTITUTE

CROSS REFERENCE TO RELATED APPLICATIONS

This application is a continuation of U.S. application Ser. No. 07/706,894 filed May 29, 1991, now abandoned.

FIELD OF THE INVENTION

This invention relates to a modified starch composition. More particularly, the present invention is directed to a microcrystalline particulate starch composition useful as a fat substitute in processed reduced calorie foods.

BACKGROUND AND SUMMARY OF THE INVENTION

The food industry has invested in a significant research and development effort to identify food ingredient products that can exhibit a sensory perception of fattiness in foods without the high calorie content of common oil and fat ingredients. For example, certain protein and carbohydrate compositions are proposed as fat replacements in U.S. Pat. No. 4,911,946 and references identified therein. Carbohydrates and proteins have less than one-half of the calories of available metabolic energy than carbohydrates on a per gram basis. Two significant proteins, namely whey protein and egg white protein, in the form of microspheres of about 1–10 microns have been made by at least two companies for use as fat mimics. The above referenced U.S. Pat. No. 4,911,946 suggests that small substantially spherical carbohydrate-based particles, including small whole starch granules in the 0.1–3 micron diameter size range, are acceptable fat mimics.

This invention relates to a granular starch-derived microcrystalline starch composition for use as a fat mimic. The microcrystalline starch composition is prepared by disintegration of partially hydrolyzed (microporous) starch granules by use of mild acid hydrolysis or by mechanical action, such as that of a ball mill or a roll mill. The resulting microparticulate starch product comprises irregularly shaped starch particles which, when used as a substitute for at least a portion of the fat content of processed foods, imparts the sensory perception of fattiness with less calorie content and without compromise of other organoleptic qualities of the modified food product. The microcrystalline particulate starch composition in accordance with this invention is optionally treated with a surface modifying agent to complement the functional qualities of the starch composition.

DETAILED DESCRIPTION OF THE INVENTION

Microporous starch granules prepared by the action of acid or amylase on granular starch are well known in the literature. See, for example, the description in "Photomicrographs" in my book, *Starch Chemistry and Technology*, 2nd Edition, 1984, Academic Press, Inc., New York, N.Y. A process for preparing surface modified microporous granular starch is described in my U.S. Pat. No. 4,985,082, issued Jan. 15, 1991, the disclosure of which is expressly incorporated herein by reference. Microporous starch granules can thus be prepared by partial hydrolysis by acid or, more preferably, enzyme action on granular starch for a period of time sufficient to solubilize up to about 10 to about 50% of their mass. Starch hydrolysis does not occur at equal rates at all points on the granule surface. Hydrolysis occurs preferentially, more precisely at a faster rate, at the more amorphous regions on the granule surface. Regions of higher crystallinity are denser and thus the starch molecules are less accessible to the amylolytic action of starch hydrolyzing enzymes or even acid hydrolysis. The resultant microporous granular starch compositions are thus comprised of the more crystalline regions of the granules in a network of "bridges" of adjacent unhydrolyzed portions of the starch granule.

In accordance with the present invention, a microcrystalline particulate composition is prepared by disintegration of the resultant weakened granular structure by mechanical force such as by crushing/shearing in a ball mill or roll mill. Alternatively the microporous granular starch can be disintegrated by mild acid hydrolysis. The present starch composition comprises the resultant irregularly shaped super-crystalline domains of starch granules with appendant remains of the starch "bridges" broken during disintegration of the microporous granular starch. The microcrystalline starch composition is thus characterized as comprising birefringent starch particles with protruding remains of the starch "bridges", which give the appearance, under microscopic examination, of a diffuse outer surface.

Particle size distribution in the microcrystalline starch composition of this invention depends to some extent on the source of the starch (thus the size distribution of the native granular starch starting material) and processing conditions, e.g., degree of hydrolysis in producing the microporous starch intermediate and the means/extent of disintegration of that intermediate. Typically the average particle size ranges from about 0.1 to about 10 microns, but most are within the range of about 0.1 to about 6 microns.

Optionally, the microcrystalline starch composition can be chemically modified to optimize the functional characteristics associated with its use as a fat substitute for processed foods. Chemical treatments which work to increase the lipophilic character of the starch composition are particularly useful. Chemical modification of the starch composition can be effected either by adsorption of surface modifying agents or by reaction of the starch with starch reactive chemical reagents which form covalent bonds with the starch substrate. Such starch modifying agents include chemical cross-linking agents which can be employed to enhance the firmness and gelation temperature of the modified microcrystalline starch particles. Any of a wide variety of food acceptable starch modifying agents can be employed, including more particularly, those described in my U.S. Pat. No. 4,985,082, incorporated herein by reference. Thus, a greater degree of structural integrity can be introduced by treating the starch with an effective amount of a bifunctional starch-reactive chemical cross-linking agent. Any of a variety of art-recognized starch cross-linking agents, including those recognized as food-acceptable by the Food and Drug Administration, can be used. Suitable cross-linking agents include phosphates such as sodium trimetaphosphate, dicarboxylic acids derivatives, particularly $C_2$–$C_6$ dicarboxylic acids including maleic and glutaric acid, phosphorous oxychloride, epichlorohydrin and $\beta,\beta$-dichlorodiethyl ether. Surface characteristics can be adjusted by treatment with surface modifying agents which can either be adsorbed onto the surface of the starch or covalently bound to the starch. For example, the surface of the starch can be rendered more lipophilic by derivatizing starch molecules on the starch surface with long fatty acid chains, for example, by reacting the starch with stearyl- or octenyl-succinic acid anhydride thereby esterifying the starch with long chain fatty acids or derivatives thereof or by etherification with long chain fatty halides. Treatment with acetic anhydride will also provide some lipophilic character to the starch but a higher level of derivitization is required. Chemical modification of the starch composition can also be effected by adsorption of surface modifying agents. Thus, for example, the starch can be treated with solutions of polymers, such as methylcellulose, polyvinyl alcohol, poly-N-vinyl-2-pyrrolidone, polyacrylamide, carboxymethylcellulose, carragenan or other food grade gums. The optional chemical modification of the microcrystalline starch composition in accordance with this invention can be performed on the microporous granular starch intermediate product before the disintegration step or on the microcrystalline composition after disintegration of the microporous starch intermediate. Alternatively, the starch can be subjected to treatment with two or more chemical modifying agents at the same or at different points in the process of their manufacture.

In carrying out the present invention, the microporous starch intermediate is preferably prepared by the partial enzymatic hydrolysis of granular starch from any one of a wide variety of sources including corn, wheat, or potato, with a raw starch hydrolyzing enzyme such as alpha amylase or glucoamylase. Typically the granular starch is hydrolyzed at a temperature of about 25°–65° for a period of about ½ to about 4 hours. The microporous granular starch product is dried, optionally subjected to chemical modifications, and thereafter disintegrated mechanically or chemically to form the microcrystalline starch composition of the present invention. The product microcrystalline starch composition is recovered by product handling/processing techniques commonly utilized in the production of art-recognized chemically modified granular starches. The microcrystalline starch composition can be also subjected to size classification processing using, for example, cyclone separators to produce microcrystalline starch fractions having improved food functional characteristics deriving from their enhanced particle size homogeneity.

The product microcrystalline starch in accordance with this invention is utilized as a food ingredient and a substitute for all or a portion of the fat content in processed foods to provide a low calorie form of the food product with minimal compromise of organoleptic quality. The microcrystalline starch composition of the present invention mimics the mouth feel and other functional characteristics of fats in processed food products and offers a significant improvement over reduced-calorie fat substitutes known in the art.

Although the invention has been described in detail with reference to its preferred embodiments, variations and modifications exist within the scope and spirit of the invention as defined in the following claims.

What is claimed:

1. A method for preparing a starch composition useful as a fat substitute in reduced calorie foods, said method comprising the steps of partially hydrolyzing granular starch to form microporous starch granules, chemically modifying the starch to cross-link it by reacting it with a bifunctional starch reactive cross-linking agent selected from the group consisting of sodium trimetaphosphate, dicarboxylic acid derivatives, particularly $C_2$-$C_6$ dicarboxylic acids including maleic and glutaric acid, phosphorus oxychloride, epichlorohydrin and $\beta,\beta$-dichlorodiethyl ether, or to modify its surface characteristics by adsorption of surface modifying agents selected from the group consisting of methylcellulose, polyvinyl alcohol, poly-N-vinyl-2-pyrrolidone, polyacrylamide, carboxymethylcellulose, and carrageenan, or by reaction of the starch with a starch reactive etherifying or esterifying agent which forms a covalent bond with the starch, and disintegrating the microporous starch granules to form subgranular fragments of crystalline starch having an average particle size of about 0.1 to about 10 microns.

2. The method of claim 1 wherein the microporous granular starch is formed by action of an amylase enzyme on granular starch.

3. The method of claim 1 wherein the microporous granular starch is formed by action of a mineral acid on granular starch.

4. The method of claim 1 wherein the microporous granular starch is mechanically disintegrated to form the starch composition.

5. The method of claim 2 wherein the microporous granular starch is mechanically disintegrated to form the starch composition.

6. The method of claim 1 wherein the chemical modification step comprises the step of reacting the starch with a bifunctional starch-reactive chemical cross-linking agent.

7. The method of claim 1 wherein the chemical modification step comprises the step of reacting the starch with a starch-reactive etherifying or esterifying agent which forms a covalent bond with the starch to increase the lipophilicity of the starch.

* * * * *